# United States Patent [19]

Goto et al.

[11] Patent Number: 5,840,934
[45] Date of Patent: Nov. 24, 1998

[54] PROCESS FOR PRODUCING EPOXIDIZED PRODUCT OF OLEFINS

[75] Inventors: Fumisato Goto, Tsukuba; Satoru Shibata, Naka-gun; Toshio Sasaki; Kozo Tanaka, both of Tsukuba, all of Japan

[73] Assignee: Sumitomo Chemical Company, Limited, Osaka, Japan

[21] Appl. No.: 874,246

[22] Filed: Jun. 13, 1997

[30] Foreign Application Priority Data

Jun. 14, 1996 [JP] Japan ................................. 8-153823

[51] Int. Cl.$^6$ .................................................. C07D 301/19
[52] U.S. Cl. ............................................ 549/529; 549/531
[58] Field of Search ...................................... 549/529, 531

[56] References Cited

U.S. PATENT DOCUMENTS 5,354,875  10/1994  Nemeth et al .......................... 549/529

FOREIGN PATENT DOCUMENTS

| | | |
|---|---|---|
| 0049806A | 4/1982 | European Pat. Off. . |
| 0100119A | 2/1984 | European Pat. Off. . |
| 0132294A | 1/1985 | European Pat. Off. . |
| 0787681A | 8/1997 | European Pat. Off. . |
| 55-018646 | 5/1980 | Japan . |
| 56-096720 | 8/1981 | Japan . |
| 57-092506 | 6/1982 | Japan . |
| 63-156005 | 6/1988 | Japan . |
| 01023401 | 5/1989 | Japan . |
| 04005028 | 1/1992 | Japan . |

*Primary Examiner*—Amelia Owens
*Attorney, Agent, or Firm*—Stevens, Davis, Miller & Mosher, L.L.P.

[57] ABSTRACT

Disclosed is a process for producing an epoxidized product of olefins, which comprises oxidizing olefins in the presence of an oxidizing catalyst, using an alcohol medium solution of hydrogen peroxide produced by catalytically reacting hydrogen with oxygen in an alcohol medium.

According to the present invention, an epoxidized product of olefins can be produced by using an alcohol medium solution of hydrogen peroxide in high selectivity without requiring an aqueous hydrogen peroxide solution of high concentration and producing a large amount of by-products.

7 Claims, No Drawings

PROCESS FOR PRODUCING EPOXIDIZED PRODUCT OF OLEFINS

BACKGROUND OF THE INVENTION

1. Field of the Invention

The present invention relates to a process for producing an epoxidized product of olefins. More particularly, it relates to a process for producing an epoxidized product of olefins, which comprises reacting olefins with hydrogen peroxide in an alcohol medium.

2. Description of Related Art

An epoxidized product of olefins, particularly propylene oxide, is one of important industrial products as a raw material of propylene glycol, polypropylene glycol, etc.

As a general industrial process of producing propylene oxide, for example, a chlorohydrin process, a Halcon process and a peracetic acid process are known but these processs had a problem that, since a large amount of by-products are produced, the disposition of the resultant by-products is required.

To the contrary, a process of using hydrogen peroxide in the presence of a titanium compound has an advantage that a large amount of by-products are not produced (Japanese Patent Kokoku No. 4-5028 and U.S. Pat. No. 5,354,875). For example Japanese Patent Kokoku No. 4-5028 discloses that an olefin can be epoxidized in high yield and high selectivity by using crystalline titanosilicate as a catalyst and hydrogen peroxide as an oxidizing agent in an alcohol medium. Incidentally, hydrogen peroxide in an aqueous medium was used as the oxidizing agent.

When the medium of hydrogen peroxide is an aqueous medium, it was necessary to use after diluting the aqueous medium with an organic solvent (e.g. alcohol, etc.) as an efficient medium in the epoxidation reaction. For example, it was necessary that an aqueous 30 wt % hydrogen peroxide solution is diluted with methanol to give a 5 wt % hydrogen peroxide solution containing methanol as a main solvent and the resulting hydrogen peroxide solution is used for the epoxidation reaction. Therefore, in order to maintain a concentration of hydrogen peroxide used for the epoxidation reaction at a predetermined concentration, it was necessary to previously produce an aqueous hydrogen peroxide solution of higher concentration.

Since the aqueous hydrogen peroxide solution of higher concentration requires a concentration step, the process becomes complicated, which results in high price. Furthermore, it had the following problems. That is, there is a large risk because of high concentration and a step of diluting with an alcohol is required and, furthermore, a large amount of by-products such as glycol, etc. are produced because a large amount of water is contained.

By the way, a most popular industrial process of producing hydrogen peroxide is an autoxidation process by using an alkyl anthraquinone at present. However, this process has such problems that the process becomes complicated because a lot of steps such as reduction/oxidation of the alkyl anthraquinone and extraction/separation, purification and concentration of the resultant hydrogen peroxide are required, and loss of the alkyl anthraquinone and deterioration of a reducing catalyst take place.

In order to solve these problems, there is suggested a process of bringing hydrogen into contact with oxygen in an aqueous medium in the presence of a platinum group metal to directly synthesize hydrogen peroxide (Japanese Patent Kokoku Nos. 55-18646 and 1-23401 and Japanese Patent Kokai (laid-open) No. 63-156005). For example, Japanese Patent Kokai (laid-open) No. 63-156005 discloses that an aqueous hydrogen peroxide solution of high concentration can be produced from hydrogen and oxygen in an aqueous medium containing an acid and a halide ion in the presence of a platinum group metal supported on a carrier. However, these processs are processs of producing hydrogen peroxide in the aqueous medium and, as described above, in order to use as the oxidizing agent of the epoxidation of the olefin after diluting with the organic solvent, it was necessary to produce hydrogen peroxide of higher concentration.

In order to obtain an aqueous hydrogen peroxide having a concentration as high as possible by means of these processs, it was necessary to react under high pressure condition. It can not be said that the production of hydrogen peroxide under high pressure condition is industrially efficient because the cost of various equipments becomes higher. High pressure condition had a problem in view of the safety because the reaction between hydrogen and oxygen is liable to cause explosion. Therefore, it becomes important to accomplish a process capable of producing hydrogen peroxide efficiently even under low pressure condition and capable of using hydrogen peroxide efficiently for the epoxidation reaction of the olefin.

Japanese Patent Kokai (laid-open) No.57-92506 discloses that alcohol, ketone, ether, ester and amide can be used as a reaction medium and methanol is more preferable. However, in order to efficiently obtain a hydrogen peroxide solution, it was necessary to allow formaldehyde to coexist in the reaction medium to prevent decomposition of the produced hydrogen peroxide. Accordingly, there was a problem that a step of adding formaldehyde and a step of removing/purifying formaldehyde are required, so the process becomes complicated. Furthermore, a possibility that formaldehyde inhibits a catalytic activity is undeniable.

The present inventors have intensively studied about a process of producing an epoxidized product of olefins which do not cause the above-described problems. As a result, an epoxidized product of olefins can be produced by using an alcohol medium solution of hydrogen peroxide in high selectivity without requiring an aqueous high concentration hydrogen peroxide solution and producing a large amount of by-products. Thus, the present invention has been accomplished.

SUMMARY OF THE INVENTION

That is, the present invention provides a process for producing an epoxidized product of olefins, which comprises oxidizing olefins in the presence of an oxidizing catalyst, by using an alcohol medium solution of hydrogen peroxide produced by catalytically reacting hydrogen with oxygen in an alcohol medium.

DETAILED DESCRIPTION OF THE INVENTION

The present invention will be explained in detail hereinafter.

(1) Production of Hydrogen Peroxide

In the present invention, it is necessary to use an alcohol medium as a reaction medium upon production of hydrogen peroxide. The alcohol medium in the present invention means an alcohol or a mixed solution containing the alcohol as a main component. In case of the mixed solution containing the alcohol as the main component, the other component includes ketone, ether, ester, amide, water, etc. As the alcohol medium, an alcohol single medium is preferably used. As the alcohol, for example, methanol, ethanol, isopropanol, butanol, ethylene glycol, etc. may be used. Among them, methanol and ethanol are preferable, and methanol is more preferable.

In the present invention, it is preferred to react in the presence of a platinum group metal or a compound of the platinum group metal when hydrogen peroxide is produced by catalytically reacting hydrogen with oxygen.

It is preferred to use those produced by catalytically reacting hydrogen with oxygen in an alcohol medium in the presence of a halide of a platinum group metal, as hydrogen peroxide. Therefore, it is possible to produce hydrogen peroxide, which is suitable as a reagent for epoxidation reaction of olefins, without requiring an aqueous high concentration hydrogen peroxide solution and adding an acid, a compound which is dissociated to form a halogen ion, or formaldehyde, etc.

Examples of the platinum group metal include rhodium, iridium, platinum, palladium, etc. Among them, platinum or palladium is preferable, and palladium is used more preferably. As the halogen compound, for example, a fluorine compound, a chlorine compound, a bromine compound and an iodine compound are used. Among them, the chlorine compound or bromine compound is preferably used. Specific examples of the halogen compound of the platinum group metal include rhodium chloride, rhodium bromide, iridium chloride, iridium bromide, platinum chloride, platinum bromide, palladium fluoride, palladium chloride, palladium bromide, palladium iodide, transdichlorodiaminepalladium etc. Among them, palladium chloride and palladium bromide are particularly preferred.

The reaction can be conducted in a continuous or batch-wise manner. As a reaction device, a suspension bed or fixed bed type can be used. An amount of the halogen compound of the platinum group metal used is not specifically limited, but is normally from 1 mg to 10 g, preferably from 10 mg to 10 g, based on 100 ml of the reaction medium in case of the suspension bed type. The halogen compound of the platinum group metal may take any form such as fine powder, pellet, etc. Among them, a fine powder is preferable and those having a surface area of 0.01 to 10000 m$^2$/g are preferably used. The halogen compound of the platinum group metal can be used alone or by supporting on a suitable carrier. Generally, the yield of hydrogen peroxide per weight of the metal is larger when the halogen compound is supported.

Examples of the carrier include alumina, silica, titania, magnesia, zirconia, ceria, zeolite, graphite, active carbon, silica gel, hydrated silicic acid, silicon carbide, etc. Among them, alumina, silica, titania, zeolite, graphite and active carbon are preferably used.

As a process of supporting on the carrier, for example, there is a process of suspending the carrier in a solution of the halogen compound of the platinum group metal, followed by evaporation to dryness. The process may be any process capable of supporting, and is not specifically limited.

It is preferred to use those produced by catalytically reacting hydrogen with oxygen in an alcohol medium containing an acid and a halogen compound of an alkaline metal or an alkaline earth metal in the presence of a platinum group metal, as hydrogen peroxide. Also in this case, it is not necessary to use an aqueous hydrogen peroxide solution of high concentration and to add an additive such as formaldehyde. Therefore, it is preferable.

Specific examples of the platinum group metal include rhodium, iridium, platinum, palladium, etc. Among them, palladium is preferable. The platinum group metal may be used alone or by supporting by various carriers. As the platinum group metal supported, various metals are commercially available and commercially available products may be used.

The platinum group metal may take any form such as fine powder, pellet, etc. The reaction can be conducted in a continuous or batch-wise manner. As a reaction device, a suspension bed or fixed bed type can be used. These are not specifically limited. An amount of the platinum group metal used is not specifically limited, but is normally from 1 mg to 10 g, preferably from 10 mg to 10 g, based on 100 ml of the reaction medium in case of the suspension bed type.

Examples of the acid used in this process include sulfuric acid, hydrochloric acid, phosphoric acid, etc. These acids may be used in combination thereof. A concentration of the acid is preferably from 0.001 to 1N, more preferably from 0.01 to 1N.

Specific examples of the halogen compound of the alkaline metal and alkaline earth metal include sodium fluoride, sodium chloride, sodium bromide, sodium iodide, potassium chloride, potassium bromide, magnesium chloride, magnesium bromide, calcium chloride, calcium bromide, etc. Among them, the chloride, bromide or iodide of the alkaline metal is preferably used. The chloride or bromide of the alkaline metal is more preferable, and the bromide of the alkaline metal is most preferable.

An amount of the halogen compound of the alkaline metal or alkaline earth metal used is preferably from $1\times10^{-6}$ to $1\times10^{-3}$N, more preferably from $1\times10^{-5}$ to $1\times10^{-3}$N.

It is preferred to neutralize hydrogen peroxide, produced by catalytically reacting hydrogen with oxygen in an alcohol medium containing an acid and a halide of an alkaline metal or an alkaline earth metal in the presence of a platinum group metal, with a base before using in the following step of producing the epoxidized product of olefins because the selectivity of the epoxidized product becomes higher. As the base, for example, a solution of a hydroxide of the alkaline metal or alkaline earth metal is preferable. Specific examples thereof include sodium hydroxide, potassium hydroxide, calcium hydroxide, rubidium hydroxide, etc. The hydroxide of the alkaline metal is used more preferably. These bases are normally used in the form of an aqueous solution or an alcohol solution. For example, a high concentration solution of 1 to 20N is preferable because the concentration of hydrogen peroxide after neutralizing is not drastically lowered. An amount of the base added is an equivalence point or less. The more, it is closed to the equivalence point, the better.

In the reaction for producing hydrogen peroxide according to the present invention, a partial pressure ratio of oxygen to hydrogen is preferably within the range from 1:50 to 50:1. It is also possible to react by diluting with an inert gas or to react by using air in place of oxygen. It is preferred to react under the condition which is out of the range of explosion in view of the safety. The reaction temperature is preferably from 5° to 60° C., more preferably from 10° to 50° C. The reaction pressure is not specifically limited, but is preferably within the range from atmospheric pressure to 150 kg/cm$^2$.G, more preferably from 5 to 50 kg/cm$^2$.G.

In the present invention, the alcohol medium solution of hydrogen peroxide thus obtained is used in an epoxidation reaction step of olefins as the following step. It is preferred to use it in the following step after removing a solid component in the reaction medium. A process of removing the solid component is not specifically limited, and examples thereof include processs such as decantation, filtration, etc.

(2) Epoxidation of Olefins

A catalyst used in the production of propylene oxide in the present invention may be any oxidizing catalyst, and is not specifically limited. In addition to $MoO_3$, $V_2O_5$, $WO_3$ and titanosilicate, $TiO_2$ supported on the carrier such as $SiO_2$, etc. are preferable. Among them, titanosilicate is more preferable. The titanoslicate in the present invention refers to those obtained by substituting a part of silicons, which constitute a crystal lattice in a crystalline $SiO_2$ having a zeolite structure, with titanium. A process for producing titanosilicate is not specifically limited, but the production example thereof include Japanese Patent Kokai (laid-open) No. 56-96720. It is preferred that an atomic ratio of Si to Ti in titanosilicate is from 10 to 1000.

An amount of the oxidizing catalyst used is not specifically limited, but is preferably from 1 mg to 10 g based on 100 ml of the reaction medium in case of the suspension bed type. The catalyst may take any form such as fine powder, pellet, etc. The reaction can be conducted in a continuous or batch-wise manner. As a reaction device, a suspension bed or fixed bed type can be used. These are not specifically limited.

As the olefins to be epoxidized by the process of the present invention, for example, ethylene, propylene, allyl chloride, 2-butene, 1-octene, 1-tridecene, mesityl oxide, isoprene, cyclooctene and cyclohexene are preferable. Among them, ethylene and propylene are more preferable, and propylene is most preferable.

The reaction temperature is preferably from 5° to 150° C., more preferably from 30° to 100° C. When the reaction is conducted at high temperature, e.g. a boiling point of the medium or higher, it is normally conducted under pressure. When using a gaseous olefin, the reaction pressure is not specifically limited but is preferably from atmospheric pressure to 100 $kg/cm^2$.G, more preferably from 3 to 30 $kg/cm^2$.G.

According to the present invention, it is possible to effectively use cheap and low concentration hydrogen peroxide which is not required to be concentrated. Therefore, it becomes possible to allow the epoxidation reaction to proceed in high selectivity without requiring an aqueous hydrogen peroxide solution of high concentration. As a result, it becomes possible to produce an epoxidized product of olefins, e.g. propylene oxide, cheaply.

EXAMPLES

The following Examples and Comparative Examples further illustrate the present invention in detail but are not to be construed to limit the scope thereof.

The concentration of hydrogen peroxide in the Examples was determined by the iodimetric titration. A potentiometric automatic titrator AT-310 manufactured by KYOTO ELECTRONICS MANUFACTURING Co., Ltd. was used for titration.

The quantitative determination of the epoxidation reaction product was conducted by gas chromatography, and a selectivity of propylene oxide was calculated from the following equation:

(Selectivity % of propylene oxide)=(number of mols of propylene oxide produced)/(number of mols of hydrogen peroxide consumed)×100

The conversion of hydrogen peroxide was calculated from the following equation:

(Conversion of hydrogen peroxide)=(number of mols of hydrogen peroxide consumed)/(number of mols of hydrogen peroxide before reaction)×100

Furthermore, the specific surface area was measured by using Flow Sorb II, 2300 type, manufactured by Micromeritics Instruments Co.

Example 1

(1) Production of Hydrogen Peroxide

An inner vessel having a internal volume of 300 ml, wherein 30 mg of $PdBr_2$ (specific surface area: 0.4 $m^2/g$, manufactured by NACALAI TESQUE, INC.) and 120 ml of methanol was charged, was fit with an autoclave having an internal volume of 400 ml. A hydrogen gas and an oxygen gas were introduced in a flow rate of 80 ml/min and 800 ml/min, respectively, using a gas blowing tube. A nitrogen gas was introduced into a vapor phase part in a flow rate of 2500 ml/min and a pressure was maintained so that an autoclave internal pressure becomes 9 $kg/cm^2$.G. A reaction vessel was maintained at 20° C. by external cooling. The concentration of hydrogen peroxide in the reaction solution after 2 hours have passed since the beginning of the reaction was 0.15% by weight.

(2) Production of Propylene Oxide

A hydrogen peroxide methanol solution obtained in the above item (1) (48 g) and 200 mg of titanosilicate (Atomic ratio of Si to Ti: 50, manufactured by N. E. Chemcat Corporation) were charged in an autoclave having an internal volume of 125 ml, and then a propylene gas was introduced under pressure so that an internal pressure thereof becomes 4 $kg/cm^2$.G. The conversion of hydrogen peroxide after stirring at the reaction temperature of 40° C. for 1 hour was 99% and the selectivity of propylene oxide was 70%.

Example 2

(1) Production of Hydrogen Peroxide

An inner vessel having a internal volume of 300 ml, wherein 30 mg of a Pd powder (specific surface area: 10.8 $m^2/g$, manufactured by TANAKA KIKINZOKU KOGYO K.K.) and a mixed methanol solution of 5 ml of a 0.0012N-NaBr methanol solution, 5 ml of a 1.2N-$H_2SO_4$ and 110 ml of methanol were charged, was fit with an autoclave having an internal volume of 400 ml. A hydrogen gas and an oxygen gas were introduced in a flow rate of 80 ml/min and 800 ml/min, respectively, using a gas blowing tube. A nitrogen gas was introduced into a vapor phase part in a flow rate of 2500 ml/min and a pressure was maintained so that an autoclave internal pressure becomes 9 $kg/cm^2$.G. A reaction medium was maintained at 20° C. by external cooling. The concentration of hydrogen peroxide in the reaction solution after 2 hours have passed since the beginning of the reaction was 0.35% by weight.

(2) Production of Propylene Oxide

A solution (48 g) prepared by adding 3.1 ml of an aqueous 2N-NaOH solution to the hydrogen peroxide methanol solution obtained in the above item (1), followed by stirring, and 200 mg of titanosilicate (Atomic ratio of Si to Ti: 50, manufactured by N. E. Chemcat Corporation) were charged in an autoclave having an internal volume of 125 ml, and then a propylene gas was introduced under pressure so that an internal pressure thereof becomes 4 kg/cm$^2$.G. The conversion of hydrogen peroxide after stirring at the reaction temperature of 40° C. for 1 hour was 65% and the selectivity of propylene oxide was 95%.

Example 3

Using a solution prepared by adding 2.5 ml of an aqueous 2N-NaOH solution to the hydrogen peroxide methanol solution obtained by producing under the same condition as that of Example 2 (1) followed by stirring, the reaction was conducted under the same condition as that of Example 2(2). The conversion of hydrogen peroxide after stirring at the reaction temperature of 40° C. for 1 hour was 98% and the selectivity of propylene oxide was 27%.

What is claimed is:

1. A process for producing an epoxidized product of olefins, which comprises oxidizing olefins in the presence of an oxidizing catalyst by using an alcohol medium solution of hydrogen peroxide produced by catalytically reacting hydrogen with oxygen in an alcohol single medium without requiring formaldehyde in the presence of a halogen compound of the platinum group metal.

2. The process according to claim 1, wherein the oxidizing catalyst is titanosilicate.

3. The process according to claim 1, wherein the olefin is propylene.

4. The process according to claim 1, wherein the halogen compound of the platinum group metal is a halogen compound of the platinum group metal supported on a carrier.

5. The process according to claim 4, wherein the halogen compound of the platinum group metal is a halogen compound of palladium or platinum.

6. The process according to claim 4, wherein the halogen compound of the platinum group metal is palladium chloride or palladium bromide.

7. The process according to any one of claim 1, wherein the alcohol medium is methanol.

* * * * *